United States Patent
Mine et al.

(10) Patent No.: US 6,239,316 B1
(45) Date of Patent: May 29, 2001

(54) OPTICALLY ACTIVE SECONDARY ALCOHOL AND PROCESS FOR THE PRODUCTION THEREOF

(75) Inventors: Takakiyo Mine; Tomoyuki Yui, both of Tsukuba (JP)

(73) Assignee: Mitsubishi Gas Chemical Company Inc, Tokyo (JP)

( * ) Notice: Subject to any disclaimer, the term of this patent is extended or adjusted under 35 U.S.C. 154(b) by 0 days.

(21) Appl. No.: 09/365,844

(22) Filed: Aug. 3, 1999

(30) Foreign Application Priority Data

Aug. 17, 1998 (JP) .................................. 10-230689

(51) Int. Cl.⁷ .................................. C07C 43/10
(52) U.S. Cl. ............................................. 568/678
(58) Field of Search ............................................. 568/678

(56) References Cited

U.S. PATENT DOCUMENTS

| | | | | |
|---|---|---|---|---|
| 2,808,442 | * | 10/1957 | Smith et al. | 260/611 |
| 4,226,637 | * | 10/1980 | Linden et al. | 106/308 |
| 5,349,110 | * | 9/1994 | Knifton | 568/678 |
| 5,629,423 | * | 5/1997 | Klein et al. | 544/48 |

FOREIGN PATENT DOCUMENTS

| | | |
|---|---|---|
| 0301587 | 12/1992 | (EP) . |
| 0517504 | 7/1998 | (EP) . |
| 64 3154 | 1/1989 | (JP) . |
| 1316339 | 12/1989 | (JP) . |
| 1316367 | 12/1989 | (JP) . |
| 1316372 | 12/1989 | (JP) . |
| 2225434 | 9/1990 | (JP) . |
| 2229128 | 9/1990 | (JP) . |
| 2282340 | 11/1990 | (JP) . |
| 5-65486 | 3/1993 | (JP) . |
| 8337555 | 12/1996 | (JP) . |

OTHER PUBLICATIONS

M. Johno, et al. "Ferroelectric Liquid Crystals", J. Org. Syn. Chem. Soc., 47(6), pp. 568–582 (1989).

J. Yaozhong, et al., "Assymetric Synthesis XXI. Enantioselective Reduction of Ketones Catalyzed By New (4S,5R)–4, 5–Diphenyl–1,3,2–Oxazaborolidine", Tetrahedron: Assymetry, 5(7), pp. 1211–1214 (1994).

T. Kitazume, et al., "A Microbially Based Approach for the Preparation of Chiral Molecules Possessing The TriFluoromethyl Group", J. Org. Chem., 52, pp. 3211–3217 (1987).

A.M. Klibanov, et al., "Resolution of Racemic Mixtures Via Lipase Catalysis in Organic Solvents", J. Am. Chem. Soc., 107, pp. 7072–7076 (1985).

Patent Abstracts of Japan, vol. 98, No. 9, Jul. 31, 1998.

* cited by examiner

*Primary Examiner*—Howard C. Lee
*Assistant Examiner*—Leigh C. Maier

(57) ABSTRACT

An R-configuration or S-configuration optically active secondary alcohol of the general formula (1), $$CH_3C^*H(OH)(CH_2)_mOCH(C_nH_{2n+1})_2 \qquad (1)$$

wherein C* is an asymmetric carbon atom, m is an integer of 1 to 3, and n is an integer of 1 to 3, and a process for the production thereof, comprising optical resolution of a corresponding racemic alcohol by asymmetric transesterification, specifically using a lipase derived from *Candida antarcia* microorganism. The present invention can provide the novel optically active secondary alcohol having a methyl group on an asymmetric carbon and an alkoxy terminal having branched alkyl chains formed of the same numbers of carbon atoms, and an economical and simple process for the production thereof.

6 Claims, No Drawings

OPTICALLY ACTIVE SECONDARY ALCOHOL AND PROCESS FOR THE PRODUCTION THEREOF

DETAILED DESCRIPTION OF THE INVENTION

1. Field of the Invention

The present invention relates to a novel optically active secondary alcohol having a methyl group on an asymmetric carbon and an alkoxy terminal having branched alkyl chains formed of the same numbers of carbon atoms and a process for the production thereof.

2. Prior Art

While optically active compounds have been used in the fields of medicaments and agricultural chemicals, they have been attracting attention as functional materials such as ferroelectric liquid crystal and organic non-linear materials in recent years. For example, in the field of organic non-linear materials, molecules of organic materials preferably have an asymmetric center for producing secondary non-linear optical effect (e.g., Yamaguchi, Nakako and Fueno, "Kagaku" (Chemistry) 42 (11), 757 (1987)). In the field of ferroelectric liquid crystal compounds, liquid crystal compounds are required to have an optically active structure for a liquid crystal exhibiting ferroelectricity (e.g., Johno, Fukuda, Journal of Organic Synthesis Chemistry Society, 47 (6), 568 (1989)).

In recent years, further, anti-ferroelectric liquid crystal is attracting considerable attention, while the anti-ferroelectric liquid crystal compounds are required to have an optically active structure like a ferroelectric liquid crystal. In the above fields, optically active 2-butanol, 2-octanol, 2-methyl-1-butanol or an amino acid derivative has been used as an optically active source.

However, the obtained optically active materials are limited in characteristics so long as the above optically active compounds are used as sources.

In the field of ferroelectric liquid crystals, attempts are recently being vigorously made to synthesize ferroelectric liquid crystals from the following alcohols in which a fluoroalkyl group is substituted on their asymmetric carbon atoms as optically active alcohols (e.g., JP-A-64-3154, JP-A-1-316339, JP-A-1-316367, JP-A-1-316,372, JP-A-2-225,434 and JP-A-2-229,128).

(1) $CF_3C^*H(OH)CH_2COOC_2H_5$
(2) $CF_3C^*H(OH)CH_2CH_2OC_2H_5$
(3) $CF_3C^*H(OH)CH_2CH_2CH_2OC_2H_5$
(4) $CF_3C^*H(OH)CH_2CH_2CH_2CH_2OC_2H_5$
(5) $CF_3C^*H(OH)C_6H_{13}$
(6) $CF_3C^*H(OH)C_8H_{17}$
(7) $C_2F_5C^*H(OH)C_8H_{17}$

Ferroelectric liquid crystal compounds synthesized from the above alcohols all give high spontaneous polarization and relatively fast response speeds since a fluoroalkyl group having high electro-negativity is substituted on the asymmetric carbon of each. It is also known that a liquid crystal compound synthesized from the above (5), (6) or (7) is likely to give a liquid crystal having an anti-ferroelectric phase, and these alcohols are attracting attention as particularly characteristic alcohols.

Further, with regard to the process for the synthesis of an optically active alcohol of $CF_3C^*H(OH)(CH_2)_mOC_nH_{2n+1}$ (in which m is an integer of 2 to 7 and n is an integer of 1 to 4), the present inventors made close studies on the process for the synthesis thereof and a liquid crystal produced therefrom, and it was found that the above alcohol gives very useful anti-ferroelectric liquid crystal or ferroelectric liquid crystal (JP-A-5-65486 and JP-A-8-337555).

When an anti-ferroelectric liquid crystal or a ferrielectric liquid crystal is synthesized from an optically active alcohol containing an asymmetric carbon having a trifluoromethyl group substituted thereon, the so-synthesized liquid crystal shows high spontaneous polarization. When the spontaneous polarization is high, the response speed is fast, which is advantageous in this respect. With an increase in the spontaneous polarization, however, the interaction with an insulating film and an aligned film in an electrode cell is intensified, and the deformation of hysteresis of voltage-optical transmission increases to an extraordinary extent. There is therefore liable to be caused a problem that no drive margin is permitted.

There is therefore desired a liquid crystal which shows a small spontaneous polarization and, on the other hand, which is free of problems in view of a response speed and a tilt angle, and is desired an optically active secondary alcohol which can give substantially such a property.

An optically active secondary alcohol can seem to be produced by various methods.

In view of economic performance, however, it is not expedient to use an optically active compound as a starting material, since it is expensive.

On the other hand, an optically active alcohol may be also produced by asymmetric synthesis. For example, it is thinkable to employ a method in which an optically active alcohol is produced by preparing a corresponding ketone compound as a precursor and asymmetrically reducing it in the presence of an asymmetric reduction catalyst. In this case, however, the asymmetric reduction catalyst is very expensive, and further, a product having a high optical purity cannot be always obtained. Moreover, only one optical active compound of either an R-configuration compound or an S-configuration is obtained.

For example, there is known a method in which a prochiral ketone is asymmetrically reduced in the presence, as a catalyst, of a complex in which (1R,2R)-1,2-diphenyl-2-aminoethanol as a ligand coordinates to a boron atom (J. Yaozhong, et al., Tetrahedron: Asymmetry, 5(7), 1211 (1994)).

The above method is remarkably effective for aromatic ketones. However, it cannot be said that the above method is effective for aliphatic ketones, since obtained enantiomers have a very low optical purity.

In another method, it is thinkable to asymmetrically hydrolyze a proper ester as a precursor for an optically active compound, such as an acetate. An enzyme is used as an effective asymmetric hydrolysis agent. The asymmetric hydrolysis of an acetate with lipase has been proposed by Kitazume et al (T. Kitazume et al., J. Org. 52, 3211 (1987), JP-A-2-282340).

According to Kitazume et al, the acetate of the formula, $CF_3CH(OCOCH_3)C_nH_{2n+1}$ is asymmetrically hydrolyzed in the presence of lipase MY in a phosphoric acid buffer solution.

However, the capability of the lipase MY recognizing asymmetry is greatly dependent upon the chemical structure of a compound to be hydrolyzed. And, the optical purity data of obtained hydrolysis products greatly vary from 55 to 98%ee depending upon chemical structures of hydrolyzed compounds as is shown in Table 1 in the above literature by Kitazume et al.

The above results show that it is difficult to pre-calculate whether or not an object compound can be effectively asymmetrically hydrolyzed, and that it is found only after a reaction whether or not an alcohol as an end product having a high optical purity can be obtained.

Further, there is another serious problem that the capability of asymmetry recognition is not at all exhibited when some substituent is on an asymmetric carbon.

For example, lipase MY exhibits the capability of remarkably high asymmetry recognition in the asymmetric hydrolysis of $CF_3C^*H(OCOCH_3)(CH_2)_5OC_2H_5$. However, lipase MY does not show any asymmetry recognition for an ester of a secondary alcohol, $CH_3C^*H(OCOCH_3)C_6H_{13}$, in which a methyl group is substituted on the asymmetric carbon.

In addition, an optically active secondary alcohol is also produced by a method in which a secondary racemic alcohol is asymmetrically trans-esterified in the presence of a proper enzyme and the optical resolution thereof is carried out.

For example, there is a method of asymmetric trans-esterification in the presence of a lipase (derived from porcine pancreas) in an organic solvent (A. M. Klibanov, et al., J. Am. Chem. Soc. 1985, 107, 7072).

However, no lipase having high activity and high enantio-selectivity has been known. The asymmetric hydrolysis using an enzyme or the optical resolution by asymmetric trans-esterification is advantageous in that both R-configuration and S-configuration optically active alcohols are easily obtained.

The present invention has been made under the above circumstances, and it is an object of the present invention to provide a novel optically active secondary alcohol having a methyl group on an asymmetric carbon and an alkoxy terminal having branched alkyl chains formed of the same numbers of carbon atoms, and an effective process for the production thereof.

Means to Solve the Problems

That is, according to the present invention, there is provided an R-configuration or S-configuration optically active secondary alcohol of the general formula (1),

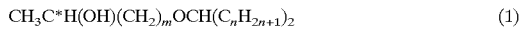

wherein C* is an asymmetric carbon atom, m is an integer of 1 to 3, and n is an integer of 1 to 3.

An alcohol of the above general formula (1) in which m is 2 and an alcohol of the above general formula (1) in which n is 1 are preferred. The optically active secondary alcohol has a high optical purity and preferably has an optical purity of at least 90%ee.

According to the present invention, further, there is provided a process for the production of an R-configuration or S-configuration optically active secondary alcohol by optical resolution of a racemic alcohol of the general formula (2),

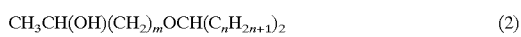

wherein m is an integer of 1 to 3 and n is an integer of 1 to 3, characterized in that the optical resolution is carried out by asymmetric trans-esterification of the said racemic alcohol.

In the above process of the present invention, vinyl propionate is suitable as an esterification agent using for the above asymmetric trans-esterification of the said racemic alcohol.

In the present invention, it is preferred to use lipase derived from *Candida antarcia* microorganism as a catalyst for the above asymmetric trans-esterification, and an immobilized enzyme prepared by immobilizing the above lipase in a porous acrylic resin is particularly preferred. As the above lipase, the immobilized enzyme is commercially available from Novo Nordisk Co., Ltd.

The lipase derived from *Candida antarcia* microorganism, used in the present invention, is excellent in that it has remarkably high reactivity per unit amount and has high enantio selectivity, i.e., high selectivity to convert R-configuration to a propionate ester selectively. Further, it has remarkably high reactivity as compared with lipase derived from porcine pancreas and lipase derived from Pseudomomas microorganism which are known to have capability of the optical resolution of a secondary alcohol, and even the small amount thereof can show high reactivity.

The use amount of lipase is in proportion to a reaction rate, and the amount thereof is therefore determined depending upon a determined reaction time period. Generally, however, the amount of the above lipase for use per mole of the racemic alcohol as a precursor is preferably in the range of from 0.1 to 10 g.

The reaction temperature for the above asymmetric trans-esterification is preferably between 20° C. and 40° C. for attaining a sufficient reaction rate and a sufficient enantio selectivity.

Effect of the Invention

The present invention can provide a novel optically active secondary alcohol having a methyl group on an asymmetric carbon and having an alkoxy terminal having branched alkyl chains formed of the same numbers of carbon atoms, the optically active secondary alcohol having a high optical purity, and an economical and simple process for the production thereof.

EXAMPLES

The present invention will be explained in detail with reference to Examples hereinafter, while the present invention shall not be limited thereto.

Example 1

Preparation of R-(+)-4-isopropyloxybutan-2-ol (formula (1): m=2, n=1 (E1))

(1) Preparation of 4-isopropyloxybutan-2-ol (racemic compound)

40 Grams of a 12% $NaBH_4$ solution (NaOH solution) was gradually added dropwise to 0.35 mol of commercially available 4-isopropyloxybutan-2-ol. The mixture was stirred at room temperature for 3 hours, then, water was added, and the mixture was extracted with ether. An ether layer was washed with 6N hydrochloric acid, and then washed with water until the ether layer almost showed neutrality, and the resultant ether layer was washed with a saturated sodium chloride aqueous solution.

The above-prepared ether layer was dried over anhydrous sodium sulfate, and the ether was distilled off to give a crude product at a yield of 73. The crude product was purified by distillation, to give an end product (50 Torr, 94° C., yield 70%).

(2) Preparation of R-(+)-4-isopropyloxybutane-2-propionate

13 Grams of vinyl propionate and 300 mg of lipase (Novozym 435) were added to 0.22 mol of the racemic secondary alcohol obtained in the above (1), and the mixture was stirred at room temperature for 24 hours.

After completion of the reaction, the lipase was filtered off, and the remainder was washed with hexane. Then, the hexane, alcohol as a raw material, etc., were distilled off.

The above-prepared product was purified by silica gel column chromatography to give an oily end product (20 Torr, 93° C.: yield 88%) and S-(-)-4-isopropyloxybutan-2-ol (yield 60%).

(3) Preparation of R-(+)-4-isopropyloxybutan-2-ol 0.09 Mol of the R-(+)-4-iropropyloxybutane-2-propionate obtained in the above (2) was added to a solution of 7 g of potassium hydroxide in 20 ml of water/methanol (1/3), and the mixture was stirred at room temperature for 1 hour. After completion of the reaction, the reaction mixture was extracted with ether, an organic layer was washed with water and with a saturated sodium chloride aqueous solution, and the washed organic layer was dried over anhydrous sodium sulfate. The anhydrous sodium sulfate was filtered off, and then the ether was distilled off to give an end product (32 Torr, 83° C., yield 68%).

(4) Preparation of high-optical-purity R-(+)-4-isopropyloxybutane-2-propionate

8 Grams of vinyl propionate and 200 mg of lipase (Novozym 435) were added to 0.06 mol of the optically active alcohol having an optical purity of 83%, obtained in the above (3), and the mixture was stirred at room temperature for 24 hours.

After completion of the reaction, the lipase was filtered off, the remainder was washed with hexane, and the hexane was distilled off. The resultant product was purified by silica gel column chromatography to give an oily end product (20 Torr, 93° C.: yield 95%).

(5) Preparation of high-optical-purity R-(+)-4-isopropyloxybutan-2-ol 0.05 Mol of the R-(+)-4-iropropyloxybutane-2-propionate obtained in the above (4) was added to a solution of 4 g of potassium hydroxide in 12 ml of water/methanol (1/3), and the mixture was stirred at room temperature for 1 hour. After completion of the reaction, the reaction mixture was extracted with ether, an organic layer was washed with water and with a saturated sodium chloride aqueous solution, and the washed organic layer was dried over anhydrous sodium sulfate. The anhydrous sodium sulfate was filtered off, and then the ether was distilled off to give an end product (32 Torr, 83° C., yield 76%).

Table 1 shows NMR spectrum data of the end product (E1) obtained in Example 1.

Further, the end product (E1) obtained in Example 1 was measured for an optical purity by the following method.

The obtained optically active alcohol was converted to an acetate with pyridine/anhydrous acetic acid. The obtained acetate was analyzed with gas chromatograph (CP Cyclodex β236M) for the analysis of optically active compounds, and the optically active alcohol was determined for a purity on the basis of a peak area ratio of two enantiomers. Further, the optically active alcohol was measured for a specific rotation in the presence of chloroform as a solvent.

Table 2 shows the results.

TABLE 1

| Example No. (Symbol) | Proton number and Chemical structure | | | | | | Chemical shift (ppm) | | | | | |
|---|---|---|---|---|---|---|---|---|---|---|---|---|
| | | | | | | | 1 | 2 | 3 | 4 | 5 | 6 |
| 1 (E1) | 1 | 2 | 3 | 4 | 5 | 6 | 1.2 | 4.0 | 1.2 | 1.2 | | 3.6 |
| | $CH_3C^*H(OH)(CH_2)_2OCH(CH_3)_2$ | | | | | | | | | | | |

TABLE 2

| Example No. | Chemical structure | Optical purity | Specific rotation*1 |
|---|---|---|---|
| 1 (E1) | $CH_3C^*H(OH)(CH_2)_2OCH(CH_3)_2$ | 95.2 % ee | +2.7° |

*1: Measured with sodium D ray at 29° C.

What is claimed is:

1. An R-configuration or S-configuration optically active secondary alcohol of the general formula (1), $$CH_3C^*H(OH)(CH_2)_mOCH(C_nH_{2n+1})_2 \qquad (1)$$

wherein C* is an asymmetric carbon atom, m is 2 and n is an integer of 1 to 3.

2. The optically active secondary alcohol of claim 1, wherein n in the general formula (1) is 1.

3. The optically active secondary alcohol of claim 1, which has an optical purity of at least 90%ee.

4. The optically active secondary alcohol of claim 1, which has an R-configuration.

5. The optical active secondary alcohol of claim 1, wherein n in the general formula (1) is 2.

6. The optical active secondary alcohol of claim 1, wherein n in the general formula (1) is 3.

* * * * *